United States Patent [19]
Peng et al.

[11] Patent Number: 6,069,180
[45] Date of Patent: May 30, 2000

[54] SINGLE STEP SYNTHESIS GAS-TO-DIMETHYL ETHER PROCESS WITH METHANOL INTRODUCTION

[75] Inventors: Xiang-Dong Peng, Orefield; Andrew Wilson Wang, Alburtis; Bernard Allen Toseland, Allentown, all of Pa.

[73] Assignee: Air Products and Chemicals, Inc., Allentown, Pa.

[21] Appl. No.: 09/213,480

[22] Filed: Dec. 17, 1998

[51] Int. Cl.$^7$ .................................................. C07C 27/00
[52] U.S. Cl. ........................... 518/700; 518/714; 518/728
[58] Field of Search .................... 518/700, 728, 518/714

[56] References Cited

U.S. PATENT DOCUMENTS

| | | | |
|---|---|---|---|
| 4,536,485 | 8/1985 | Topp-Jorgensen | 502/62 |
| 5,753,716 | 5/1998 | Peng et al. | 518/700 |

FOREIGN PATENT DOCUMENTS

| | | | |
|---|---|---|---|
| 3181435 | 8/1991 | Japan | C07C 43/04 |
| 10182529 | 7/1998 | Japan . | |
| 9623755 | 8/1996 | WIPO | C07C 41/01 |

OTHER PUBLICATIONS

"A Novel Mechanism of catalyst deactivation in Liquid Phase Synthesis Gas–to–DME Reactions", X. D. Peng, B. A. Toseland, R. P. Underwood, Stud. Surf. Sci. Catal. vol. 111, 1997, p. 175.

Dybkjaer and Hansen (Natural Gas Conversion IV, Studies in Surface Science and Catalysis, vol. 107, p. 99, 1997, Elsevier Science B. V.).

Xu et al. (Applied Catalysis A: General 149, 1997, p. 303–309).

*Primary Examiner*—Gary Geist
*Assistant Examiner*—J. Parsa
*Attorney, Agent, or Firm*—Robert J. Wolff

[57] ABSTRACT

A process is set forth for converting synthesis gas into dimethyl ether (DME) in a single step comprising contacting the synthesis gas with a bifunctional catalyst system having a methanol synthesis functionality and a methanol dehydration functionality. In particular, the present invention is an improvement to said process for increasing the stability of the bifunctional catalyst system, particularly when the process is conducted in the liquid phase. The improvement comprises introducing a methanol containing stream into the DME reactor such that the methanol concentration throughout the DME reactor is maintained at a concentration greater than 1.0%, generally between 4.0% and 8.0%. In one embodiment of the present invention, the methanol containing stream comprises at least a portion of the byproduct methanol from the DME reactor such that said portion of byproduct methanol is introduced into the DME reactor as a recycle stream.

9 Claims, 1 Drawing Sheet

6,069,180

SINGLE STEP SYNTHESIS GAS-TO-DIMETHYL ETHER PROCESS WITH METHANOL INTRODUCTION

CROSS-REFERENCE TO RELATED APPLICATIONS

Not applicable.

STATEMENT REGARDING FEDERALLY SPONSORED RESEARCH OR DEVELOPMENT

This invention was made under DOE Contract DE-FC22-95PC93052 and is subject to government rights arising therefrom.

BACKGROUND OF THE INVENTION

Single-step conversion of synthesis gas (a gas comprising hydrogen and carbon monoxide and often referred to as "syngas") to dimethyl ether (DME) is very attractive as a route for indirect coal liquefaction, natural gas utilization, and production of synthetic liquid fuels or fuel additives. By converting synthesis gas to methanol and then further converting the methanol to dimethyl ether in the same reactor, the overall synthesis gas conversion is freed from the equilibrium constraint imposed by the thermodynamics of methanol synthesis alone. The prior art teaches a number of process schemes, many of which use gas phase, fixed bed reactors. The bifunctional catalyst system used in these schemes may be either a single catalyst with activity both for methanol synthesis and dehydration of methanol to dimethyl ether, or a mixed bed of methanol synthesis and methanol dehydration catalysts. However, liquid phase processes using a liquid phase reactor such as a slurry bubble column reactor (SBCR) offer significant advantages in heat transfer (which translates into process efficiency), operability and catalyst replacement. Therefore, it is highly desirable to use liquid phase technology for synthesis gas conversion to dimethyl ether. Liquid phase syngas-to-DME processes face one problem: there is a detrimental interaction between commercial $CuO/ZnO/Al_2O_3$ methanol synthesis catalysts and most, if not all, effective methanol dehydration catalysts. This interaction is evidenced by loss of activity of one or both catalysts. ("A Novel Mechanism of catalyst deactivation in Liquid Phase Synthesis Gas-to-DME Reactions", X. D. Peng, B. A. Toseland, R. P. Underwood, Stud. Surf. Sci. Catal. Vol.111, 1997, pg 175). The prior art does not teach any methanol dehydration catalysts which demonstrate acceptable catalyst stability over the full range of commercially attractive conditions. Furthermore, the prior art does not teach single-particle, dual-functional catalysts for synthesis gas to dimethyl ether which are not subject to this detrimental interaction.

In the absence of a single catalyst or mixture of catalysts which can achieve acceptable catalyst life, the challenge to the industry is to devise process improvements to the liquid phase syngas-to-DME process which achieve acceptable catalyst life and stability using existing catalyst systems. Furthermore, it is necessary that such improvements not significantly lessen the overall process productivity and selectivity. The present invention is such an improvement and comprises introducing a methanol containing stream into the DME reactor such that the methanol concentration throughout the DME reactor is maintained at a concentration greater than 1.0%, generally between 4.0% and 8.0%. This keeps the reactor under a methanol rich atmosphere, which helps to increase the stability of the catalyst system.

The prior art teaches both gas and liquid phase processes for single step conversion of synthesis gas to dimethyl ether. Most of these do not concern themselves with catalyst deactivation. And more importantly, none of them teach that increasing the methanol level in the reactor is beneficial to catalyst stability.

U.S. Pat. No. 4,536,485 assigned to Haldor-Topsoe addressed the issue of deactivation of alcohol dehydration catalysts via coking or polymerization of hydrocarbons. This reference teaches a treatment whereby the most strongly acidic sites on the catalyst, which are responsible for the coking and polymerization, were selectively poisoned. However, this is a different deactivation mechanism from the interaction between the methanol synthesis catalyst and the methanol dehydration catalyst described above. Even dehydration catalysts which are not subject to coking or hydrocarbon polymerization still interact negatively with the methanol catalyst, causing deactivation of one or both catalysts.

Kokai Patent Application Number 3-181435 teaches a liquid phase syngas-to-DME process and cites as one of the benefits increased catalyst life due to greater resistance to poisons present in the feed and immunity to catalyst attrition issues associated with fixed bed processes. Loss of catalyst activity due to interaction between the methanol synthesis catalyst and the methanol dehydration phases is not acknowledged in this reference nor does this reference teach the introduction of methanol to the DME reactor.

Deactivation of syngas-to-DME catalyst systems has received some attention in the open literature. Dybkjaer and Hansen (Natural Gas Conversion IV, Studies in Surface Science and Catalysis, Vol. 107, p. 99, 1997, Elsevier Science B. V.) teach that a low ratio of carbon dioxide to carbon monoxide is important for the gas phase process they developed. In particular, this reference teaches that for the manufacture of methanol or DME, a desirable property of the synthesis gas is a relatively low ratio between carbon dioxide and carbon monoxide and that a high concentration of carbon dioxide leads to unfavorable equilibrium, high water concentration in the raw product, low reaction rate and increased rate of catalyst deactivation. This reference also does not teach that introduction of methanol to the DME reactor is desirable as a means of improving catalyst stability.

Xu et al. (Applied Catalysis A: General 149, 1997, p. 303–309) teach that increasing the concentration of hydrogen in the feed to a gas phase methanol-to-DME reaction improved the stability of their Pd/silica catalyst. Once again, the mechanism of deactivation which they addressed was carbon or hydrocarbon deposition. This in no way teaches any impact of the feed composition on the extent of deactivation resulting from interactions between methanol synthesis and methanol dehydration catalysts.

WO 96/23755 assigned to Haldor-Topsoe teaches a gas phase syngas-to-DME process where methanol is present in trace amounts (0.13% or less in the examples) in the overall reactor feed due to methanol carryover from the post-reactor separation process in which unreacted synthesis gas is separated from the reactor effluent and recycled back to the DME reactor. (The methanol concentration profile throughout the actual DME reactor is not known in this reference, however, it is known that the methanol concentration in the reactor effluent is 2.05% or less in the examples.) This inadvertent recycle of trace methanol as it relates to the methanol concentration in the DME reactor is not taught as a beneficial aspect of this gas phase DME process nor does this reference recognize the relationship between the methanol concentration in the DME reactor and stability of the bifunctional catalyst system. This is not surprising since the catalyst interaction problems are typically of more concern when the DME process is conducted in the liquid phase. Indeed WO 96/23755 teaches to convert byproduct methanol to DME in an additional reactor, instead of recycling it back to the syngas-to-DME reactor.

BRIEF SUMMARY OF THE INVENTION

The present invention pertains to a single step process for converting synthesis gas into dimethyl ether (DME) in a single step comprising contacting the synthesis gas with a bifunctional catalyst system having a methanol synthesis functionality and a methanol dehydration functionality. In particular, the present invention is an improvement to said process for increasing the stability of the bifunctional catalyst system, particularly when the process is conducted in the liquid phase. The improvement comprises introducing a methanol containing stream into the DME reactor such that the methanol concentration throughout the DME reactor is maintained at a concentration greater than 1.0%, generally between 4.0% and 8.0%. In one embodiment of the present invention, the methanol containing stream comprises at least a portion of the byproduct methanol from the DME reactor such that said portion of byproduct methanol is introduced into the DME reactor as a recycle stream.

Methanol introduction into the DME reactor as per the present invention has not been taught in the prior art. This is not surprising since (i) the stabilization effect of methanol on the bifunctional catalyst system has not been known previously; and (ii) it is counter-intuitive to maintain a high methanol level in the reactor since methanol has some negative effect on the methanol synthesis equilibrium, and therefore, the overall productivity.

A key to the present invention was the recognition through extensive investigation that (i) a detrimental interaction between the methanol synthesis and methanol dehydration functionalities is a cause of catalyst deactivation under liquid phase syngas-to-DME conditions and (ii) maintaining the reactor under a methanol rich atmosphere can mitigate this detrimental interaction.

DETAILED DESCRIPTION OF THE INVENTION

Figure 1:
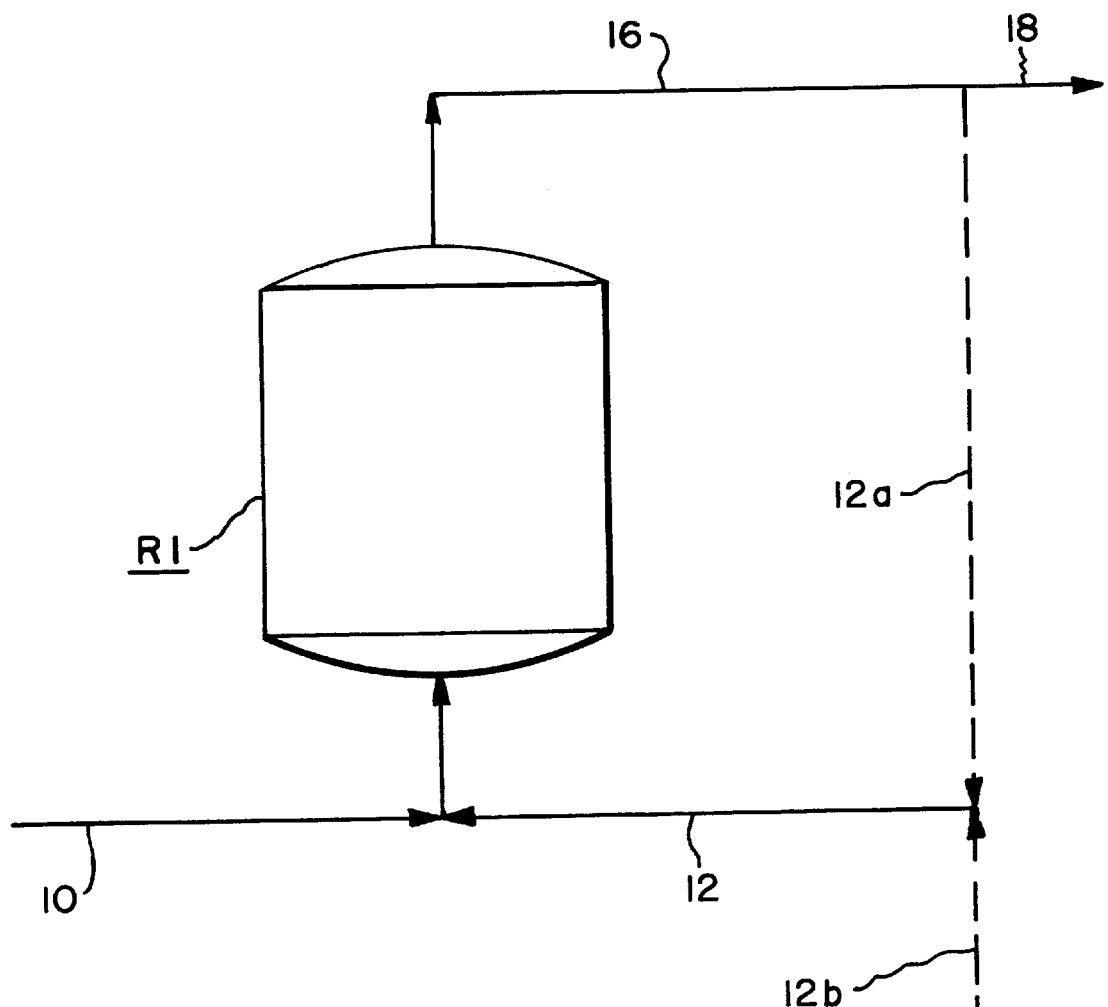
FIG. 1 is a schematic diagram illustrating the process of the present invention.

The present invention is best illustrated with reference to FIG. 1. Referring now to FIG. 1, the present invention pertains to a process for converting feedstock comprising a synthesis gas feed stream [10] comprising hydrogen and carbon monoxide into an effluent stream [16] comprising dimethyl ether (DME), unreacted synthesis gas and byproduct methanol, carbon dioxide and water. This process is a single step process and comprises contacting the synthesis gas feed [10] in a DME reactor [R1] with a bifunctional catalyst system having a methanol synthesis functionality and a methanol dehydration functionality. The present invention is an improvement to this process for increasing the stability of the bifunctional catalyst system and comprises introducing a methanol containing stream [12] into the DME reactor such that the methanol concentration throughout the DME reactor is maintained at a concentration greater than 1.0% and preferably between 3.0% and 15.0%. This keeps the reactor under a methanol rich atmosphere, which helps to maintain the activity of the catalyst system. Although methanol containing stream [12] is shown as being introduced into the DME reactor after mixing with synthesis gas feed stream [10] in FIG. 1 (mixing apparatus not shown for simplicity), methanol containing stream 12 could also be directly introduced into the DME reactor as a distinct feed stream.

As represented by stream 12a in FIG. 1, the methanol containing stream [12] can comprise at least a portion of the byproduct methanol after proper separation (separation apparatus not shown for simplicity) from the remainder [18] of the reactor effluent such that said portion of byproduct methanol is introduced into the DME reactor as a recycle stream. In this scenario, stream [12a] can also further contain unreacted synthesis gas and/or byproduct carbon dioxide and/or byproduct water, once again after proper separation from the remainder [18] of the reactor effluent.

As represented by stream [12b] in FIG. 1, the methanol containing stream [12] can also comprise make-up methanol. The make-up methanol could be in addition to, or instead of, the byproduct methanol.

The present invention is particularly applicable when the DME process is conducted in the liquid or slurry phase such that the synthesis gas is contacted with the catalyst system in powder form in a liquid phase reactor (such as a slurry bubble column reactor) containing an inert liquid medium. This is because the catalyst interaction problems are typically of more concern when the DME process is conducted in the liquid phase. Where catalyst interaction is of concern in a gas phase DME process, the reactor in the present invention can also be a gas phase reactor such as a packed bed reactor or a trickled bed reactor.

The bifunctional catalyst system can be a physical mixture containing (i) a methanol synthesis catalyst based on one or more compounds selected from the group consisting of copper, zinc, aluminum, zirconium and chromium and (ii) a methanol dehydration catalyst based on solid acid materials. The catalyst system can also be a single catalyst with both methanol synthesis and methanol dehydration functionalities.

The preferred operating conditions of the process are a pressure range from about 200 psig to 2000 psig, more preferably from about 400 psig to about 1500 psig; a temperature range from about 200° C. to about 350° C.; and a space velocity in excess of 50 standard liters of synthesis gas per kilogram of catalyst per hour, more preferably in the range from about 1,500 to about 10,000 standard liters of synthesis gas per kilogram of catalyst per hour.

In the process of the present invention, the fresh feed is typically comprised of hydrogen, carbon monoxide, carbon dioxide, water and often inert species such as nitrogen and $CH_4$. The composition of the gas can vary widely. The $H_2$:CO ratio ranges from 0.1:1 to 10:1, preferably 0.3:1 to 2:1. The $H_2O$ and $CO_2$ concentration in the feed ranges from 0 to 20 mole %, but preferably below 10 mole % and 5 mole %, respectively. The optimal composition is a function of reactor temperature, reactor pressure, space velocity, the relative activity between methanol synthesis and methanol dehydration, and the trade-off between the productivity and catalyst stability.

The positive effect of methanol introduction on the stability of the catalyst system was demonstrated in the following experiments. All runs were carried out in 300 cc stainless steel autoclave reactors at 250° C. and 750 psig. The feed and product gas were analyzed via gas Chromatograph. The catalyst system consisted of 8 grams of a commercial methanol synthesis catalyst and 2 grams of a methanol dehydration catalyst suspended in 120 grams of mineral oil. The methanol catalyst in all runs was reduced in situ using 2% $H_2$ in $N_2$, and a standard temperature ramp (about 24 hours from ambient temperature to 240° C.), followed by the introduction of the synthesis gas to the reactor. The duration of the runs was typically 180 hours.

The above reaction apparatus only allowed once-through operation. Therefore, introduction of make-up methanol, as opposed to byproduct methanol, was used to show the effect of a methanol rich environment on the stability of the catalyst system. The methanol was introduced to the feed gas through a liquid injection pump. It was vaporized in a vaporizer before it joined the synthesis gas feed and entered into the reactor.

The stability of the catalyst system is measured by the decreasing rate of the methanol synthesis rate constant, $k_m$, normalized by the initial value, with time on stream. The rate constant was calculated using the kinetic model below:

$$R_m = k_m f_{H2}^{2/3} f_{CO}^{1/3} (1-\text{appr.}) \quad [\text{mole/kg-cat./hr}]$$

where f stands for fugacity and appr. is the approach to reaction equilibrium. The deactivation of the dehydration catalyst was not a concern because it always deactivated at a rate similar to or lower than the methanol synthesis catalyst.

EXAMPLE 1

Two experiments were conducted under similar conditions using a feed gas consisting of 30%$H_2$, 66%CO, 3%$CO_2$ and 1% $N_2$, an aluminum phosphate sample as the dehydration catalyst and 2000 GHSV. The only difference was that methanol introduction was used in the second experiment at a rate of 18.5 standard cubic centimeters per minute (sccm) such that the methanol concentration throughout the DME reactor is maintained at a concentration of 4.2 mole %. (It should be noted that in a liquid phase DME reactor such as the one used in the examples herein, the methanol concentration is essentially uniform throughout due to the mixing dynamics of the reactor.) The deactivation rate of the methanol synthesis catalyst was 0.14% per hour without methanol introduction. With methanol introduction the rate decreased to 0.05% per hour. This rate is the intrinsic deactivation rate of the methanol synthesis catalyst. That is, the system achieved its best stability with the introduction of methanol.

EXAMPLE 2

Two parallel experiments were conducted, one without and the other with methanol introduction. Both used a feed gas consisting of 35%$H_2$, 51%CO, 13%$CO_2$ and 1% $N_2$, an aluminum phosphate sample as the dehydration catalyst and 6000 GHSV. The methanol introduction rate in the second experiment was 105.5 sccm such that the methanol concentration throughout the DME reactor is maintained at a concentration of 12.4 mole %. The deactivation rate of the methanol synthesis catalyst was 0.11% without methanol introduction, dropping to 0.06% per hour with methanol introduction.

EXAMPLE 3

Two parallel experiments were conducted, one without and the other with methanol introduction. Both used a feed gas consisting of 40%$H_2$, 59%CO and 1% $N_2$, an aluminum phosphate sample as the dehydration catalyst and 1600 GHSV. The methanol introduction rate in the second experiment was 13.3 sccm such that the methanol concentration throughout the DME reactor is maintained at a concentration of 6.3 mole %. The deactivation rate of the methanol synthesis catalyst was 0.16% without methanol introduction, dropping to 0.04% per hour with methanol introduction. The total productivity in these two experiments, in terms of moles of methanol plus two times moles of DME per kilogram of catalyst per hour, was 11 and 12, respectively.

EXAMPLE 4

Two parallel experiments were conducted, one without and the other with methanol introduction. Both used a feed gas consisting of 16%$H_2$, 74%CO, 6%$CO_2$ and 1% $N_2$, an aluminum phosphate sample as the dehydration catalyst and 6000 GHSV. The methanol introduction rate in the second experiment was 78 sccm such that the methanol concentration throughout the DME reactor is maintained at a concentration of 4.3 mole %. The deactivation rate of the methanol synthesis catalyst was 0.20% without methanol introduction, dropping to 0.05% per hour with methanol introduction.

EXAMPLE 5

Two parallel experiments were conducted, one without and the other with methanol introduction. Both used a feed gas consisting of 17.7%$H_2$, 64.1%CO, 10%$CO_2$ and 8% $N_2$, an aluminum phosphate sample as the dehydration catalyst and 6000 GHSV. The methanol introduction rate in the second experiment was 46.1 sccm such that the methanol concentration throughout the DME reactor is maintained at a concentration of 3.0 mole %. The deactivation rate of the methanol synthesis catalyst was 0.58% without methanol introduction, dropping to 0.05% per hour with methanol introduction.

EXAMPLE 6

Two parallel experiments were conducted, one without and the other with methanol introduction. Both used a feed gas consisting of 30%$H_2$, 66%CO, 3%$CO_2$ and 1% $N_2$, a g-alumina sample as the dehydration catalyst and 6000 GHSV. The methanol introduction rate in the second experiment was 138 sccm such that the methanol concentration throughout the DME reactor is maintained at a concentration of 7.3 mole %. The deactivation rate of the methanol synthesis catalyst was 0.20% without methanol introduction, dropping to 0.05% per hour with methanol introduction.

As shown in the examples above, methanol introduction into the syngas-to-DME reactor as per the present invention reduces the rate of catalyst deactivation to the intrinsic deactivation rate of the methanol catalyst. Therefore, the catalyst system operates without additional deactivation caused by the detrimental interaction between the methanol synthesis catalyst and the methanol dehydration catalyst. Introducing methanol in the feed gas, indeed, has some negative effects on the productivity because it impacts negatively on the methanol synthesis equilibrium. However, if one chooses the conditions correctly, this negative effect can be negligible as shown by Example 3. This includes optimal synthesis gas composition, operating conditions (reactor, temperature, pressure and space velocity) and the relative activity of methanol synthesis verses methanol dehydration.

We claim:

1. In a process for converting feedstock comprising a synthesis gas feed stream comprising hydrogen and carbon monoxide into an effluent stream comprising dimethyl ether and byproduct methanol wherein said process is a single step process comprising contacting the synthesis gas feed in a dimethyl ether reactor with a bifunctional catalyst system having a methanol synthesis functionality and a methanol dehydration functionality; the improvement to said process for increasing the stability of the bifunctional catalyst system comprising introducing a methanol containing stream into the dimethyl ether reactor such that the methanol concentration throughout the DME reactor is maintained at a concentration greater than 1.0% wherein the methanol containing stream comprises make-up methanol.

2. The process of claim 1 wherein the process is conducted in the liquid phase such that the synthesis gas is contacted with the catalyst system in powder form in a liquid phase reactor containing an inert liquid medium.

3. The process of claim 1 wherein the methanol concentration throughout the DME reactor is maintained at a concentration between 3.0% and 15.0%.

4. The process of claim 1 wherein the methanol concentration throughout the DME reactor is maintained at a concentration between 4.0% and 8.0%.

5. The process of claim 1 wherein the methanol containing stream introduced into the dimethyl ether reactor additionally comprises at least a portion of the byproduct methanol such that said portion of byproduct methanol is introduced into the DME reactor as a recycle stream.

6. The process of claim 5 wherein the effluent stream from the dimethyl ether reactor further comprises unreacted synthesis gas comprising hydrogen and carbon monoxide and wherein the methanol containing stream introduced into the dimethyl ether reactor further comprises at least a portion of the unreacted synthesis gas.

7. The process of claim 6 wherein the effluent stream from the dimethyl ether reactor further comprises byproduct carbon dioxide and byproduct water and wherein the methanol containing stream introduced into the dimethyl ether reactor further comprises at least a portion of the byproduct carbon dioxide and byproduct water.

8. The process of claim 1 wherein the methanol containing stream is introduced into the dimethyl ether reactor after mixing the methanol containing stream with the synthesis gas feed stream.

9. The process of claim 1 wherein the methanol containing stream is directly introduced into the dimethyl ether reactor as a distinct feed stream.

* * * * *